United States Patent [19]

Ring

[11] 4,010,751

[45] Mar. 8, 1977

[54] INSERTER FOR DELIVERING SOFT, DEFORMABLE TAMPONS INTO BODY CAVITIES AND THE COMBINATION OF A TAMPON THEREWITH

[75] Inventor: David F. Ring, Neenah, Wis.

[73] Assignee: Kimberly-Clark Corporation, Neenah, Wis.

[22] Filed: Sept. 11, 1975

[21] Appl. No.: 612,487

[52] U.S. Cl. .............................. 128/263; 128/270; 128/285

[51] Int. Cl.$^2$ ........................................ A61F 13/20

[58] Field of Search .................... 128/263, 270, 285

[56] References Cited

UNITED STATES PATENTS

| | | | |
|---|---|---|---|
| 2,509,241 | 5/1950 | Mende | 128/263 |
| 3,068,867 | 12/1962 | Bletzinger | 128/285 |
| 3,086,527 | 4/1963 | Forrest | 128/263 |
| 3,766,921 | 10/1973 | Dulle | 128/263 |

Primary Examiner—Aldrich F. Medbery
Attorney, Agent, or Firm—Daniel J. Hanlon, Jr.; William D. Herrick; Raymond J. Miller

[57] ABSTRACT

An inserter for delivering soft, deformable tampons into body cavities and the combination of the inserter with a suitable tampon. The inserter is particularly useful with tampons made of resiliently deformable material, such as polyurethane sponge. The inserter is made up of a pair of telescoping elements. The outer element is in the form of a tube. The inner element may also be in the form of a tube and has a main portion slidably disposed within the outer tube and a front portion comprising a smaller diameter frontal extension axially disposed on the forward end of the main portion and having a length substantially as long as the outer element when the inner element is slidably disposed therein.

In the inserter and tampon combination, the tampon is disposed within the outer tube to provide a forward head portion and a trailing skirt-like portion with at least the skirt-like portion being deformed and held in releasable compression between the frontal extension and the outer tube. The leading end of the frontal extension bears against the inside of the head portion of the tampon and when the inner element is advanced inside the outer tube, the head portion of the tampon is urged from the outer tube while the skirt-like portion is drawn from the outer tube for deposit in the vagina. Upon ejection the tampon to expands as far as the restrictive walls of the cavity permit.

14 Claims, 6 Drawing Figures

INSERTER FOR DELIVERING SOFT, DEFORMABLE TAMPONS INTO BODY CAVITIES AND THE COMBINATION OF A TAMPON THEREWITH

BACKGROUND OF THE INVENTION

It is known that absorbent tampons made of soft deformable materials, and particularly resiliently deformable materials, such as hydrophilic or mensesphilic polyurethane foams, not only provide high absorbent capacity for menstrual exudate but also protect against early leakage: This is attributed in part to the fact that uncompressed low density materials initially have high absorptive capacity and do not have to be acted upon, or depend on other expansion activating agents, to expand to useful size. In addition, the soft uncompressed materials have surface areas which more readily accept exudate and have a faster uptake than do the hardened surface areas of conventional compressed tampons. Further when resilient materials such as foams are used, the inherent springy resiliency such foams possess enable these foams to conform more readily to the multiple irregular folds, ridges and valleys of the vaginal walls when the walls are in their normal collapsed state. While high pressures exerted by the walls on any particular portion of the foam will tend to compress the foam considerably in the particular area where such pressure is exerted, immediately adjacent wall areas which exert lesser pressure, compress the foam correspondingly less, and the foam, in trying to expand to its normal uncompressed condition, will tend to fill any voids which exist thus reducing the possibility of side channel leakage and premature failure.

The main problem in utilizing resiliently deformable or other soft low density materials for internal catamenial use is how to conveniently deliver the material into the vaginal vault in a manner which overcomes the high pressures that ordinarily resist the introduction of such soft resilient material into the vaginal channel.

Such material has no significant columnar strength or integrity even when compressively confined in a tube. Accordingly, when attempts were made to use conventional delivery systems comprising a pair of telescoping tubes in which the tampon is compressively disposed in an outer tube, and an inner tube or similar pusher element is utilized to push against the bottom of the tampon to eject it into the vaginal cavity, it was found that during ejection the tampons tended to collapse or compress longitudinally, spread laterally and cause jamming within the tube so delivery was quite difficult or impossible. As a result when using ordinary tube systems one had to resort to compressing the material beyond its elastic limit or otherwise structure it in a manner to make the tampon material sufficiently dense or stiff to provide it with enough temporary structural integrity or columnar strength to be self-supporting and thus capable of being shoved out of the tube from below without the above-mentioned difficulties.

Thus, while the desirability of using a tampon which exhibits softness and resiliently expandable capabilities immediately upon insertion has been recognized, a means for delivering a tampon with such capabilities in the desired substantially uncompressed condition and in an economically feasible manner has not been satisfactorily achieved prior to this invention. Some inserter devices have been developed which mechanically spread deformable tampons at the time of insertion but none has been developed which satisfactorily holds a tampon of resiliently deformable material in temporarily deformed condition; which is capable of delivering the tampon with acceptable ease while in relatively uncompressed condition; and when resiliently compressible material is used, utilizes the inherent resiliency of the tampon itself to permit spontaneous expansion after delivery without the need for mechanically assisted deployment or for activation by the subsequent absorption of the fluids the tampons are designed to capture.

This invention is directed to a delivery system which is substantially independent on the density, softness, structural integrity or columnar strength of the tampon and yet permits relatively easy insertion of soft, readily deformable low density tampons, which may or may not be resilient, into the vaginal cavity in spite of the high pressure resistance of the walls which is normally encountered. In addition, it permits lateral positioning of the tampon after expulsion from the temporarily confining carrier member of the system.

SUMMARY OF THE INVENTION

This invention utilizes what at first glance appears to be a conventional pair of telescoping members to achieve delivery of tampons into the vagina in soft, deformable condition. That is, the delivery system comprises a pair of telescoping elements in which the outer element is in the form of a tampon confining tube or sheath and the inner element has a main tubular portion slidably disposed within the outer tube. The structure differs from the prior art in that the inner element is additionally provided with a centrally disposed frontal extension of smaller diameter than the main tubular portion. This frontal extension is dimensioned to extend through at least a major part of the length of the outer tube when the main tubular portion of the inner element is positioned therein. When combined with a tampon; the leading end of the frontal extension acts as a bearing member for the inside of the head portion of a deformable tampon, as the tampon is disposed within the outer tube, and serves to draw the remaining trailing portion of the tampon out of the tube during ejection.

In assembling the tampon and delivery system, the leading end of the frontal extension which bears against the inside of the tampon is applied to the approximate mid-point of the lower surface of an unstressed tampon and while thus positioned is pushed into the outer tube until the entire tampon is disposed inside the outer tube. When thus assembled, the head of the tampon resting on the frontal extension is compressed in thickness at its point of support and the remaining trailing portion of the tampon is circumferentially disposed around the frontal extension and resiliently compressed between the frontal extension of the inner element and the inner wall of the outer tube. When put to its intended use, the outer tube containing the tampon is first inserted into the vaginal cavity to the desired depth. The user then presses against the rear end of the inner element to slide it forward into the outer tube and eject the tampon into the vaginal cavity. During ejection the deformable tampon is worked as it slides through the confining member, loosening any temporary compression set which may have developed due to long term storage or high temperature sterilizing and the tampon then attempts to regain its original uncompressed form. The restrictive nature of the collapsed walls of vaginal cavity in their natural state will not permit the tampon to expand all the way, of course, but because the material is soft and easily deformable, the tampon will always try to expand and fill up areas where it is not restricted and thus tend to conform to most of the multiplicity of irregular shapes and configurations which the walls naturally possess. Further, as these shapes and configurations change during normal body movements, the deformable nature of the tampon permits the configuration of the tampon to give and take with these body movements and thus continue to conform to the shape of the vagina without the discomfort sometimes associated with highly compressed tampons.

At the time of ejection from the outer tube and into the vagina, the inside of the head portion of the tampon initially remains in contact with the leading end of the frontal extension of the inner element. This permits the user to employ the inserter to move the tampon laterally within the vagina to a limited extent for more comfortable positioning if desired before withdrawing the inserter device. Such after-ejection positioning is not possible with conventional tube type inserters since when the latter inserters are used all positive contact with the tampon is lost once it is ejected.

The delivery members are preferably made of a smooth flexible plastic such as low to high density polypropylene or polyethylene although other suitable materials including other plastic and paperboard may be used. The front of the outer tube may either be open or have a substantially closed configuration comprised of adjoining flexible petal shaped elements as are known in the art, and which flex open as the tampon is expelled.

The tampon may be made of any soft, deformable material, but is preferably made of sheets or strips of hydrophilic and mensesphilic polyurethane foams, many of which are known in the art. The tampon also may have innumerable shapes and configurations. The important characteristic is that the selected shape be sufficiently deformable so that when the central portion of the tampon is rested on the leading end of the frontal extension of the inner element it can be temporarily confined within the outer tube as described above. It is also preferred that when strips or sheets of foam are used, the sheets or strips be wrapped with a fluid pervious web which is of woven or non-woven construction. Preferably such wrapping is effected in a manner to permit the absorbent material to expand without restriction when wetted. Non-woven webs are usually more economical and are therefore preferred. Such wrappers add tensile strength to relatively weak foams, and in addition, they reduce the amount of friction which would otherwise be generated between the foam surface and the inner wall of the delivery tube if the wrapper were not present. The wrapper may be hydrophilic or hydrophobic.

When tampon and inserter are assembled, the tampon may be totally enclosed within the outer tube or alternatively, may have a portion partially extending out of the front end. In the latter case the exposed head portion acts as a swab during insertion, and provides added assurance against the possibility of early leakage.

Other embodiments and advantages of the invention will become apparent by reference to the accompanying drawings and detailed description.

DETAILED DESCRIPTION OF THE DRAWINGS AND PREFERRED EMBODIMENTS OF THE INVENTION

Figure 1:
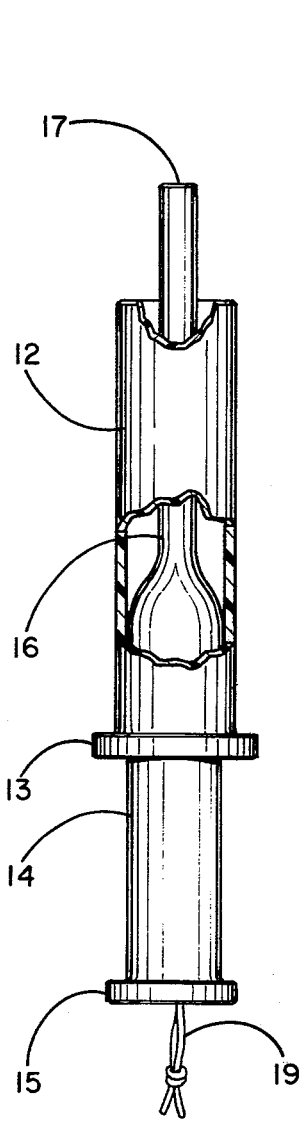
FIG. 1 is a side view of one embodiment of the inserter device of this invention with portions of the outer element partially cut away.

In FIG. 1 of the drawings there is shown a preferred embodiment of the inserter device of this invention. As shown therein the inserter is comprised of a set of telescoping elements. The outer element 12 is in the form of an open-ended tube which may have a flange 13 at its rear end to provide finger grasping means. The inner element is comprised of a main portion 14 which is in slidable engagement with the inner wall of outer element 12. Main portion 14 is of tubular configuration and has a stop flange 15 at its rear end, and has at its forward end an axially disposed frontal extension 16 of smaller diameter than main portion 14. The leading end 17 of frontal extension 16 as shown in this figure extends beyond the leading end of outer element 12. The length of the frontal extension can, of course, be adjusted to meet any selected design requirements. It should, however, be substantially as long as the outer tube when positioned therein in order to achieve complete ejection of the tampon when the inner element is advanced to its full stop position.

Figure 2:
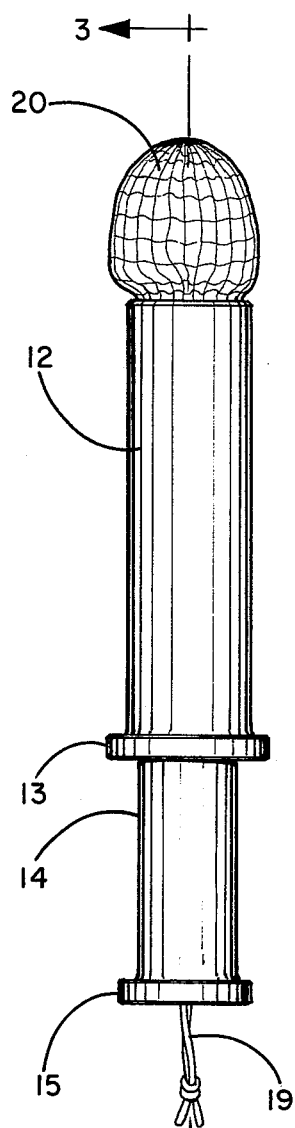
FIG. 2 is a side view of the FIG. 1 inserter device with a tampon contained therein.
Figure 3:
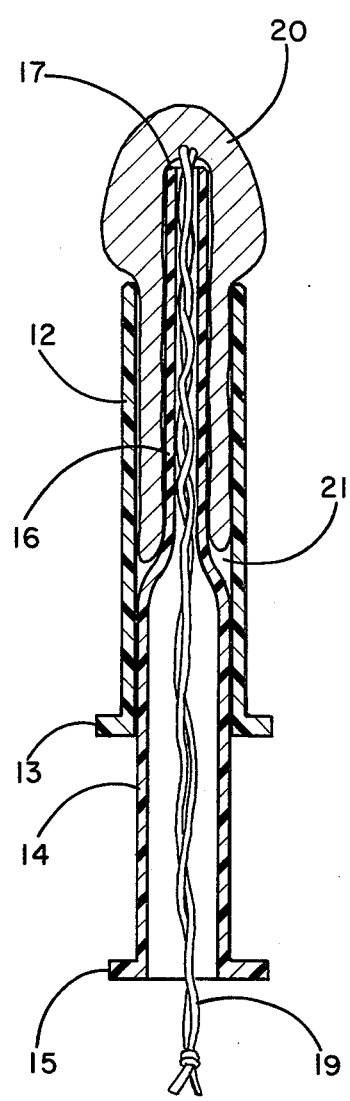
FIG. 3 is a longitudinal section taken along line 3—3 of FIG. 2.

In FIGS. 2 and 3, the inserter device of FIG. 1 is shown in combination with a resiliently deformable tampon 20. In assembling this combination, a substantially flat tampon 20 of resiliently deformable material such as thin polyurethane sponge is draped over leading end 17 of frontal extension 16 of the inner element and while supported thereon is pushed through the rear end of outer element 12. This action radially compresses tampon 20 as it is confined in the restricted narrow space 21 circumferentially defined between frontal extension 16 and the inner wall of outer tube element 12. As the tampon is pushed further into outer tube element 12 so that the head portion of tampon 20 partially protrudes from the leading end of outer tube element 12, the protruding head portion of the tampon tends to reexpand due to its inherent resilience as it escapes the confining influence of outer element 12. The remaining trailing portion of the tampon remains compressed as it is still confined in the circumferential space between frontal extension 16 and outer element 12.

When a tampon-inserter assembly of the type shown in FIGS. 2 and 3 is inserted in the vaginal cavity, the partially expanded tampon serves to swab clean any menstrual flow which may have been left on the lower vaginal areas after the previously used tampon was removed.

Figure 6:
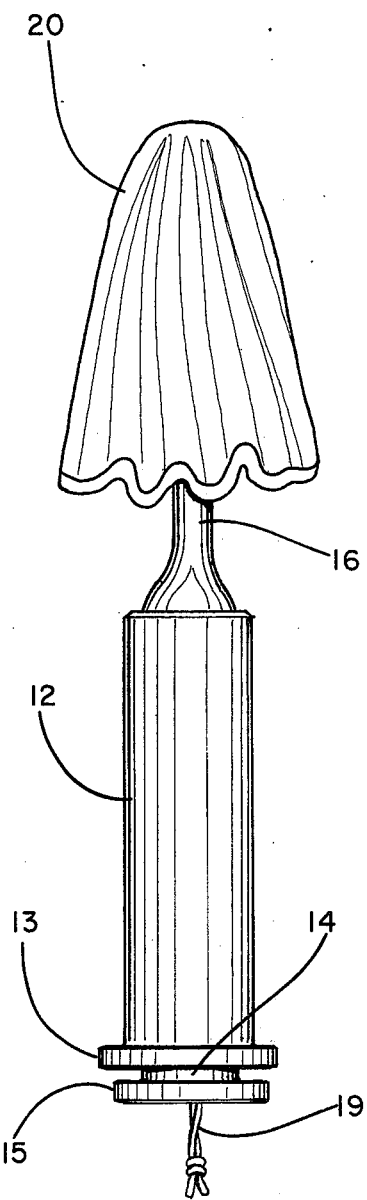
FIG. 6 is a side view similar to FIG. 2 but showing a partially reexpanded tampon as it may appear in idealized form when it begins to expand after full ejection from the inserter.

In FIG. 6, the FIG. 2 combination is shown in idealized form to depict how the tampon 20 tends to spread out after it is fully ejected from tube 12 and begins to reexpand when removed from the restrictive confines of outer tube 12. The tampon as shown here is one which is initially circular in shape and resembles a partially opened umbrella as it begins to open.

Figure 4:
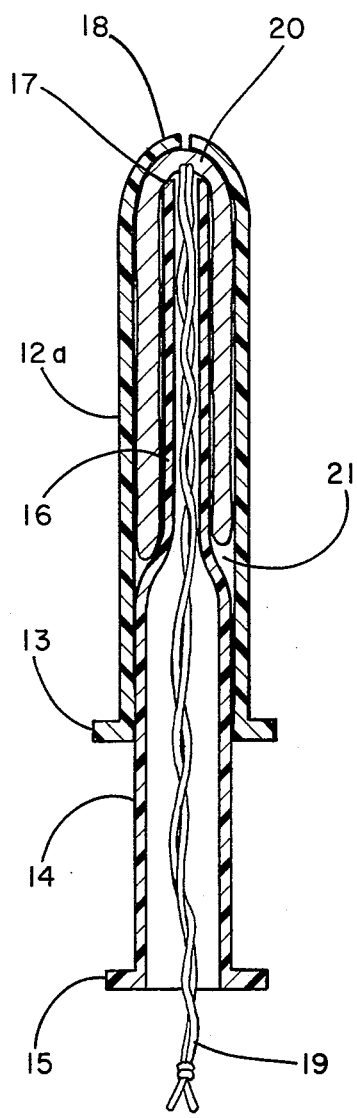
FIG. 4 is a longitudinal section similar to FIG. 3 showing another embodiment of the invention.

In FIG. 4 there is shown a structure similar to FIGS. 2 and 3 except that the front end 18 of outer tube element 12a is substantially closed and comprises a plurality of juxtaposed petal-like flexible segments 18 adapted to open outward when internal pressure is exerted against them as the contents of outer element 12a are pushed therethrough. Such closed-end inserter tubes are well known in the art and need no further detailing here. Note that in this construction the leading end 17 of frontal extension 16 will not extend beyond the end of the outer tube because frontal extension 16 is of less length than outer tube element 12 in order that the tampon will remain totally enclosed within outer element 12a before and during insertion of the delivery device into the vagina. As noted earlier, the length of the frontal extension 16 can be adjusted to meet the particular requirements of design selected by the manufacturer.

After tube element 12a is inserted and the tampon is ejected through and clear of the flexible petals as they open outward when the tampon is pushed therethrough, the tampon, when made of resiliently deformable material, will again begin to expand due to its own resilience in the same way as if the tampon were ejected from an open-ended tube as in FIG. 6. However, when a closed-end tube is used the leading end of the tampon will not be exposed during initial insertion and therefore will not have the wiping action which results when the FIG. 2 embodiment is used.

It is understood, of course, that a shorter frontal extension may be employed on the inner element even when an open-ended outer element is used. In such event, the tampon will not protrude from the front end before or during insertion and the wiping action will not be utilized. Such an arrangement, as with the closed end tube, may be considered more hygienic by the user. If this latter arrangement is used however, the user can elect to partially eject the tampon before inserting the assembly into the vagina and thus utilize the wiping action if needed or desired.

The inner element 16 in addition to having an axial frontal extension should also be provided with means for accommodating the withdrawal string 19 of the tampon. In the FIGS. 1 – 4 embodiments the string accommodating means is provided by making the frontal extension in the form of a hollow tube and the string is threaded through the entire length of that hollow space and through the hollow lower portion 14 of the inner element.

Figure 5:
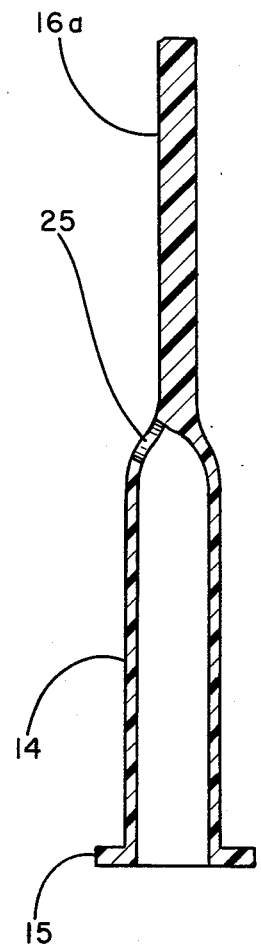
FIG. 5 is another longitudinally section showing a modified version of the inner element for the inserter device.

In FIG. 5 the frontal extension 16a is of solid construction. In this embodiment the string is draped along the side of the extension 16a and enters into the tubular main portion 14 of the inner element through aperture 25. When a solid frontal extension is used the lower portion of the inner element may also have a groove for the string or be loosely fitted in the outer element to permit the string to be disposed therebetween.

As indicated earlier, this inserter device is particularly designed for soft, low density, easily deformable tampons. Also as indicated earlier, while any soft deformable material may be used, the preferred material for the tampon is one that is resiliently deformable, i.e., it is preferred that it have an inherent springy resiliency which readily compresses under relatively light loads and then springs back to substantially its original configuration as it is worked during insertion and after the load is removed. Small pore, highly absorbent, low density polyurethane foams are particularly useful for this purpose, and since the tampons are intended primarily for catamenial use, the foam should be hydrophilic or mensesphilic.

While the preferred synthetic sponge materials such as polyurethane sponge are inherently highly resilient and when compressed tend to return to their uncompressed state when the source of compression is removed, they will sometimes take a temporary set after long term storage or when sterilization procedures are employed. However, this set is quickly and easily released with very little working such as that applied to it during the ejection process itself.

The foam may also be enclosed in a permeable wrapper material to provide additional strength. The wrapper is preferably loosely fitted to permit the foam to expand without restriction and for better conformance to varying cavity shapes. Such a wrapper also reduces frictional resistance with respect to the surfaces of the inserter with which it is in sliding contact. The wrapper may be woven or non-woven and can be hydrophilic or hydrophobic.

The particular shape of the tampon is not critical. Preferably it should be made of initially thin flat structure which can be readily deformed into a tube-fitting configuration by pushing the leading end of the frontal extension against the approximate geometric center of the shape selected. Thin flat sheets, rectangular sheets, circular sheets, irregularly shaped sheets, criss-crossed strips and the like have been found acceptable. Various preliminary folds may also be made in the tampon before being compressed into the inserter tube and readied for insertion. In use the leading end of the frontal extension is employed to push against an internal head portion of the tampon disposed as near to the leading end of the tampon as is possible when the tampon is in resiliently compressed disposition within the outer tube element. The remaining trailing portion of the tampon is thus readily drawn into the vagina while retaining its relatively uncompressed form.

Aso as indicated earlier, the inserter elements are preferably made of smooth flexible plastic material such as polyethylene or polypropylene. Nylon, polyesters and polyvinyls may also be used but generally are not as economically feasible because of fabricating cost. Paperboard tubes may also be employed.

What is claimed is:

1. An inserter device particularly adapted for delivering and depositing a structurally unattached soft, easily deformable catamenial tampon of the type equipped with a withdrawal string into body cavities with the entire inserter being adapted for removal from the cavity after such deposition, said inserter being comprised of an elongate outer element and a unitary elongate inner element in telescoping association, said outer element being in the form of a tube, said inner element having a main portion circumferentially dimensioned for slidable engagement with the inside of said tube, said main portion having on its forward end an integral axially disposed elongate extension, said extension being of smaller diameter than said main portion and said extension being of a length which extends through substantially the full length of said tube when said main portion is in slidable engagement with said tube.

2. The inserter device of claim 1 wherein said extension terminates just short of the forward end of said tube.

3. The inserter device of claim 1 wherein said extension terminates at the forward end of said tube.

4. The inserter device of claim 1 wherein said extension extends beyond the forward end of said tube.

5. The inserter device of claim 1 wherein both said main portion and said extension are hollow to accommodate the tampon withdrawal string.

6. The inserter device of claim 1 wherein said main portion is hollow, said extension is of closed construction and an aperture communicating to the hollow interior of said main portion is provided adjacent the base of said extension to accommodate the tampon withdrawal string.

7. The inserter device of claim 1 wherein said outer tube has a tapered substantially closed front end, and said tapered front end is composed of a multiplicity of flexible petal-like segments adapted to open outward when internal pressure is exerted against them.

8. In combination, a soft deformable catamenial tampon equipped with a withdrawal string, and a separate delivery system for depositing the tampon in the vagina, said tampon having a leading head portion and a trailing skirt-like portion, said delivery system including a first element comprising an outer tube and a second element comprising an inner tube in telescoping association with said outer tube, said second element having an integral small diameter frontal extension axially disposed on the forward end of said inner tube and extending substantially the full length of said outer tube when the forward end of said inner tube is in slidable association with said outer tube, said tampon being disposed within said outer tube in separable association with said second element having the interior of the head portion of said tampon in abutment with and only physically supported by the leading end of said frontal extension and having at least the skirt-like portion of said tampon circumferentially and resiliently compressed around said frontal extension while within said outer tube, said frontal extending being free of attachment to said tampon whereby when the inner element is telescopically slid into the outer element to eject the tampon therefrom and after the frontal extension urges said head portion out of said outer tube while drawing the skirt-like portion out of said outer tube to deposit said tampon in the vagina all elements of the inserter system are withdrawn leaving the deposited tampon without internal support and thereby permitting the tampon to readily conform with the internal vaginal configuration.

9. The combination of claim 8 wherein said extension terminates just short of the forward end of said outer tube.

10. The combination of claim 8 wherein said extension terminates at the forward end of said outer tube.

11. The combination of claim 8 wherein said extension extends beyond the forward end of said outer tube.

12. The combination of claim 8 wherein said extension is hollow to accommodate the tampon withdrawal string and its interior is in communication with said inner tube.

13. The combination of claim 8 wherein said extension is of closed construction and an aperture communicating to the interior of said inner tube is provided adjacent the base of said extension to accommodate the tampon withdrawal string.

14. The combination of claim 8 wherein said outer tube has a tapered substantially closed front end, and said tapered front end is composed of a multiplicity of flexible petal-like segments adapted to open outward when internal pressure is exerted against them.

* * * * *

UNITED STATES PATENT AND TRADEMARK OFFICE
CERTIFICATE OF CORRECTION

PATENT NO. : 4,010,751
DATED : March 8, 1977
INVENTOR(S) : David F. Ring

It is certified that error appears in the above-identified patent and that said Letters Patent are hereby corrected as shown below:

Column 4, line 13, "longitudinally" should read
-- longitudinal --.
Column 8, line 8, "extending" should read -- extension --.

Signed and Sealed this

Eleventh Day of October 1977

[SEAL]

Attest:

RUTH C. MASON
*Attesting Officer*

LUTRELLE F. PARKER
*Acting Commissioner of Patents and Trademarks*